(12) United States Patent
Kuhlmann

(10) Patent No.: US 9,546,754 B1
(45) Date of Patent: Jan. 17, 2017

(54) METHOD AND DEVICE FOR PREVENTING CRIMPING IN AN AIR HOSE

(71) Applicant: Richard Kuhlmann, Madison Heights, MI (US)

(72) Inventor: Richard Kuhlmann, Madison Heights, MI (US)

(*) Notice: Subject to any disclaimer, the term of this patent is extended or adjusted under 35 U.S.C. 154(b) by 0 days.

(21) Appl. No.: 15/176,249

(22) Filed: Jun. 8, 2016

(51) Int. Cl.
| *F16L 57/00* | (2006.01) |
| *F16L 57/02* | (2006.01) |
| *F16L 11/20* | (2006.01) |
| *A61M 16/00* | (2006.01) |

(52) U.S. Cl.
CPC ........... *F16L 57/02* (2013.01); *A61M 16/0003* (2014.02); *F16L 11/20* (2013.01)

(58) Field of Classification Search
CPC .... H02G 3/0481; B60R 16/0215; F16L 57/02; F16L 57/06
USPC ................. 138/129, 130, 110, 109; 428/35.1
See application file for complete search history.

(56) References Cited

U.S. PATENT DOCUMENTS

| 1,435,311 | A | * | 11/1922 | Knight | ................. | B29D 23/001 |
| | | | | | | 138/110 |
| 4,788,089 | A | * | 11/1988 | Skipper | ................... | B29C 53/12 |
| | | | | | | 138/129 |
| 4,805,933 | A | * | 2/1989 | Swisher | .................. | F16L 35/00 |
| | | | | | | 285/115 |
| 4,929,478 | A | * | 5/1990 | Conaghan | ............... | F16L 57/06 |
| | | | | | | 138/103 |
| 5,367,925 | A | * | 11/1994 | Gasparre | ................. | B25B 13/06 |
| | | | | | | 81/121.1 |
| 5,857,711 | A | * | 1/1999 | Comin-DuMong | .... | B25B 13/06 |
| | | | | | | 285/115 |
| 6,635,825 | B2 | * | 10/2003 | Adachi | ................ | H02G 3/0481 |
| | | | | | | 174/135 |
| 6,878,873 | B2 | * | 4/2005 | Fryberger, Jr. | ........... | F16L 3/26 |
| | | | | | | 138/103 |
| 7,216,678 | B2 | * | 5/2007 | Baer | ........................ | D03D 3/08 |
| | | | | | | 139/383 R |
| 7,895,716 | B2 | * | 3/2011 | Taillon | ...................... | F16L 3/14 |
| | | | | | | 174/135 |
| 9,052,042 | B2 | * | 6/2015 | May | ........................ | F16L 11/10 |
| 9,261,222 | B2 | * | 2/2016 | Lorraine | ................. | F16L 57/02 |
| 2002/0098311 | A1 | * | 7/2002 | Lindner | ............. | A44B 18/0092 |
| | | | | | | 428/40.1 |
| 2003/0079790 | A1 | * | 5/2003 | Atkinson | ............... | F16L 11/081 |
| | | | | | | 138/129 |
| 2008/0105324 | A1 | * | 5/2008 | Baer | ........................ | D03D 3/08 |
| | | | | | | 139/386 |
| 2013/0133772 | A1 | * | 5/2013 | Lorraine | ................. | F16L 35/00 |
| | | | | | | 138/110 |
| 2013/0133774 | A1 | * | 5/2013 | Lorraine | ................. | F16L 35/00 |
| | | | | | | 138/118.1 |

* cited by examiner

*Primary Examiner* — Patrick F Brinson
(74) *Attorney, Agent, or Firm* — Harness, Dickey & Pierce, P.L.C.

(57) ABSTRACT

A method and system for repairing an air hose having a first exterior diameter having a deformed or crimped portion is presented. The system includes a helical polymer member, which when in a non-deformed state, has a second inner diameter smaller than a first diameter. The helical member is disposed about the air hose on first and second sides of the deformed member. The helical member has an interior diameter equal to the first diameter when the helical member is disposed about the air hose.

4 Claims, 3 Drawing Sheets

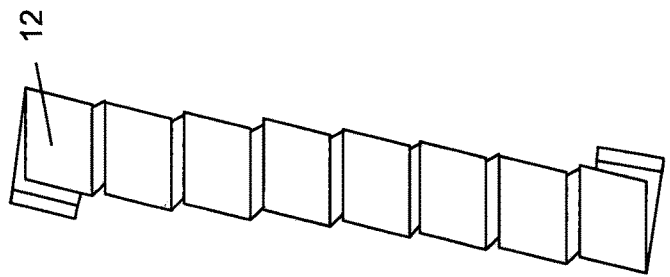
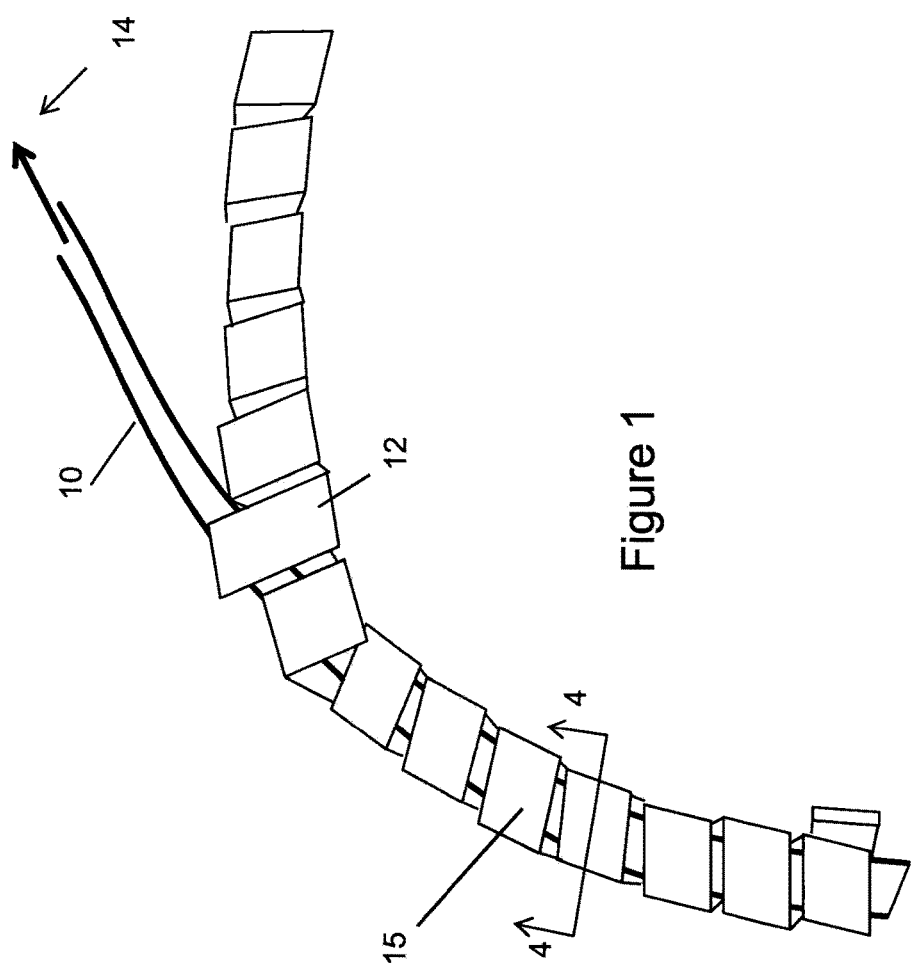
Figure 2
Figure 1

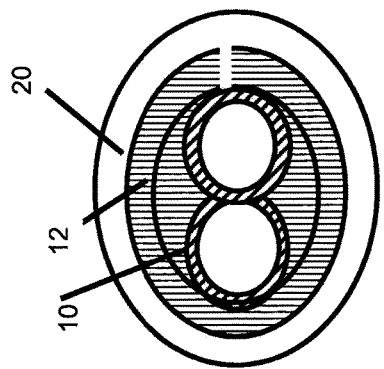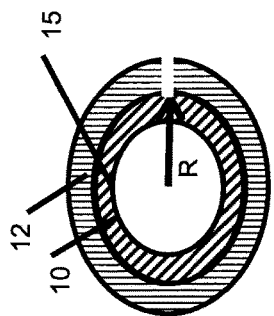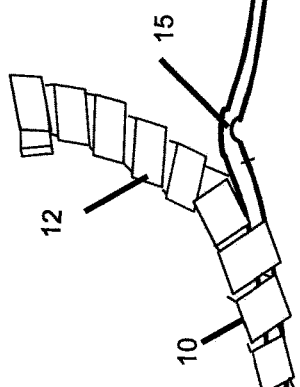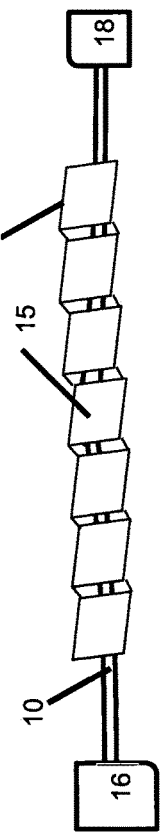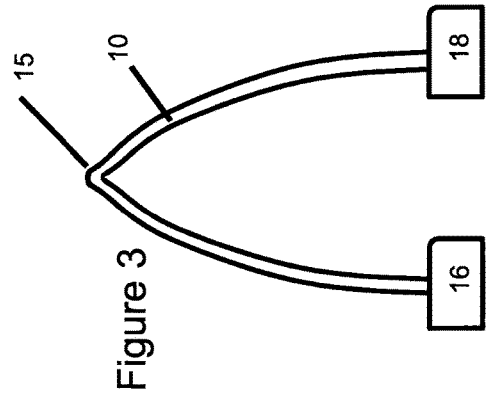

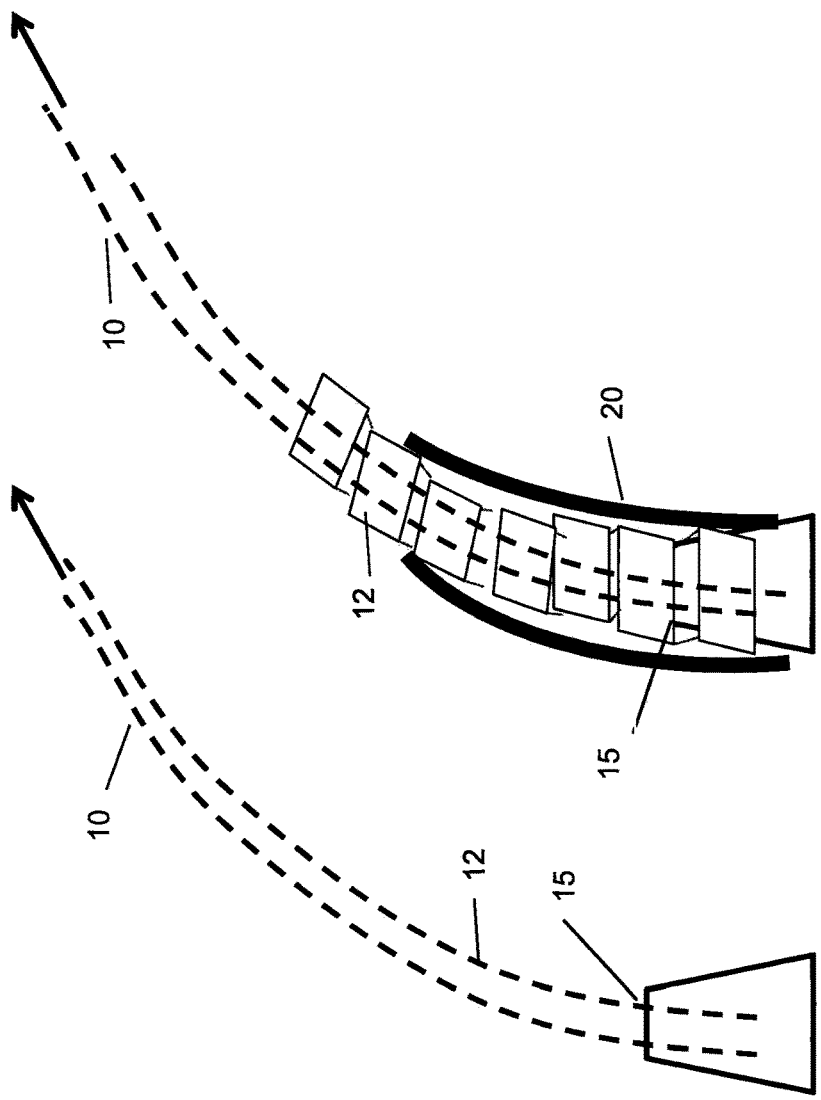

METHOD AND DEVICE FOR PREVENTING CRIMPING IN AN AIR HOSE

FIELD

The present disclosure relates to systems configured to provide oxygen to a patient and more particularly to a system for preventing the collapse of an air hose which inhibits the flow of oxygen to a patient caused by a crimped oxygen hose.

BACKGROUND

This section provides background information related to the present disclosure which is not necessarily prior art.

Patients in various treatment scenarios are provided oxygen supplementation which typically comes as flowing oxygen from a compressed source of oxygen to an appliance. This flow of oxygen allows the patient to inhale a flow of oxygen. The flow of oxygen from the source of the compressed source of oxygen, which can be a bottle or an oxygen generator, is carried to the appliance using a flexible hose. The supplementation often uses hoses which are replaced at a predetermined frequency for sanitation purposes. The replaceable hoses are susceptible to failure caused by the bending or folding of the hose. Once folded, plastic deformation within the air hose causes a weakness in the hose which leads to frequent repeated folding of the hose at the given location. This folding of the hose inhibits the flow of oxygen to a patient caused by a crimped oxygen hose which can cause discomfort and which is a safety hazard. As such, it would be desirable to have a system which prevents or repairs the disposable air hoses in a cost effecting and simple manner.

SUMMARY

This section provides a general summary of the disclosure, and is not a comprehensive disclosure of its full scope or all of its features.

According to the present teachings, a system for repairing an air hose having a first exterior diameter having a deformed portion. The system includes a helical polymer member, which when in a non-deformed state, has a second inner diameter smaller than a first diameter. The helical member being disposed about the air hose on first and second sides of the deformed member. The helical member having an interior diameter equal to the first diameter when the helical member is disposed about the air hose.

According to an alternate teaching, an air hose is provided coupled to an oxygen source coupling member. The coupling member has a first outer diameter and the air house has a second outer diameter smaller than the first diameter. The air hose has a deformed portion located adjacent to the coupling member. A helical polymer member, which when in a non-deformed state, has a third diameter smaller than the first and second inner diameter. The helical member being disposed about the air hose on a first side of the deformed member and about the air hose coupling member. The helical member having a first portion having an interior diameter equal to the first diameter equal to the outer diameter of the coupling member when the first portion of the helical member is disposed about the coupling member and a second portion disposed about the air-hose having a second helical inner diameter equal to the outer diameter of the air hose.

According to another teaching of the present invention, a method of repairing a polymer air hose is provided. The method includes, identifying a first crimp in an air hose. After identifying a crimp location in the air hose, wrapping a helical polymer member having a rectangular cross section, which when in a non-deformed state, has a second inner diameter smaller than a first diameter. The helical member being disposed about the air hose on first and second sides of the deformed member. The helical member having an interior diameter equal to the first diameter when the helical member is disposed about the air hose.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 represents a system for repairing an oxygen hose according to the present teachings;

FIG. 2 represents the polymer helical member shown in FIG. 1;

FIG. 3 depicts an air hose between an oxygen supply and a patient appliance according to the present teachings;

FIGS. 4a and 4b represent a cross sectional views of the helical member disposed about the air hose according to the present teachings;

FIGS. 5a and 5b represent the method of repairing a crimped air hose according to the present teachings; and FIGS. 6a and 6b represent the repair of an air hose coupled to an air hose coupling member.

Corresponding reference numerals indicate corresponding parts throughout the several views of the drawings.

DETAILED DESCRIPTION

Example embodiments will now be described more fully with reference to the accompanying drawings. FIG. 1 represents a system 8 for repairing an oxygen or air hose 10 according to the present teachings. Disposed about the air hose 10 is a helical member 12 which is positioned at first and second sides of a hose crimp 15. As seen in FIGS. 1 and 2, the helical member 12 has a rectangular cross section.

FIG. 2 represents the polymer helical member shown in FIG. 1. The helical polymer member 12, which when in a non-deformed state, has an inner diameter smaller than the exterior diameter of the air hose or tube 10. The helical member 12 is disposed about the air hose or tube 10 on first and second sides of the deformed tube 10. The helical member 12 having an interior diameter equal to the first diameter when the helical member 12 is disposed about the air hose 10.

FIG. 3 depicts an air hose between an oxygen supply 16 and a patient appliance 18 according to the present teachings. The oxygen supply can be an oxygen generator or a bottle of compressed oxygen. The patient appliance 18 can be a nose cannula or a face mask as is known. The flow of oxygen 14 from the source 16 of the compressed source of oxygen. is carried to the appliance using a flexible hose 10. The replaceable hoses 10 are susceptible to failure caused by the bending or folding of the hose 15. Once folded, plastic deformation within the air hose causes a weakness in the hose which leads to frequent repeated folding of the hose at the given location. This folding of the hose 15 inhibits the flow of oxygen 14 to a patient caused by a crimped oxygen hose 15 which can cause discomfort and which is a safety hazard.

FIGS. 4a and 4b represents a cross sectional view of the helical member 12 disposed about the air hose 10 and helical member 12 according to the present teachings. As shown, the helical member 12 is disposed about the air hose 10 on first and second sides of the crimped hose 15. The helical member 12 has an interior diameter, R, equal to the outer diameter of the tube 10 when the helical member is disposed about the air hose 10. The helical member 12, functions to apply compressive forces onto the exterior surface of the tube 10. FIG. 4b represents the helical member 12 disposed about a pair of tube 10.

FIGS. 5a and 5b represent the method of repairing a crimped 15 air hose or tube 10 according to the present teachings. The method includes, identifying a first crimp 15 in an air hose 10. After identifying a crimp 10 location in the air hose 10, wrapping a first portion helical polymer member 12 having a rectangular cross section and a second inner diameter smaller than the tube diameter. Wrapping a portion helical polymer member 12 about the crimped portion, and wrapping a first portion helical polymer member 12 about a second portion of the air hose 10. The construction has the helical member 12 being disposed about the air hose 10 on first and second sides of the deformed member and applies compressive forces on an exterior surface of the tube.

FIGS. 6a and 6b represent the repair or prevention of a crimp at an air hose coupled to an air hose coupling member interface. As shown in FIG. 6a, the first crimp 15 in an air hose 10 is located adjacent to the coupling member that has a diameter larger than the hose. A first portion helical polymer member 12 having a rectangular cross section and a second inner diameter smaller than the tube diameters disposed about the coupling member and over the crimp 15. A second portion is then wrapped about the hose 10 so as to provide compressive forces onto the exterior surface of the air hose 10. Optionally, an exterior polymer tube 20 can be disposed about the helical member 12. In this regard, the polymer tube can have a length that is less than the length of the helical member 12.

According to the present teachings, a system for repairing an air hose having a first exterior diameter having a deformed portion. The system includes a helical polymer member, which when in a non-deformed state, has a second inner diameter smaller than a first diameter. The helical member being disposed about the air hose on first and second sides of the deformed member. The helical member having an interior diameter equal to the first diameter when the helical member is disposed about the air hose.

According to an alternate teaching, an air hose is provided coupled to an oxygen source coupling member. The coupling member has a first outer diameter and the air house has a second outer diameter smaller than the first diameter. The air hose has a deformed portion located adjacent to the coupling member. A helical polymer member, which when in a non-deformed state, has a third diameter smaller than the first and second inner diameter. The helical member being disposed about the air hose on a first side of the deformed member and about the air hose coupling member. The helical member having a first portion having an interior diameter equal to the first diameter equal to the outer diameter of the coupling member when the first portion of the helical member is disposed about the coupling member and a second portion disposed about the air-hose having the second helical inner diameter equal to the outer diameter of the air hose.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for preventing an air hose crimp at a location adjacent to a coupling member interface, the coupling member interface having a first stiffness and a first exterior diameter and the air hose has a second stiffness and a second diameter smaller than the diameter of the first member, the system comprising:
a helical polymer member having a first length and a rectangular section, which when in a first configuration and a non-deformed state, has a second inner diameter smaller than the first exterior diameter and the second diameter, the helical member being disposed about the air coupling member and the air hose in a second configuration on first and second sides of the crimped portion, wherein a tubular member is disposed about the helical member.

2. The system according to claim 1 wherein the helical polymer member applies compressive forces onto the hose coupling member when the helical polymer member is in the second configuration.

3. The system according to claim 1 wherein the helical polymer member is disposed about a pair of air hoses.

4. The system according to claim 1 wherein the second tubular member has a second length shorter than the first length.

* * * * *